United States Patent [19]

Saell et al.

[11] Patent Number: 4,840,580

[45] Date of Patent: Jun. 20, 1989

[54] CONNECTOR ARRANGEMENT FOR A LEAD FOR AN IMPLANTABLE STIMULATION DEVICE

[75] Inventors: Goesta Saell, Norsberg; Jakub Hirschberg, Taeby, both of Sweden

[73] Assignee: Siemens AG, Berlin and Munich, Fed. Rep. of Germany

[21] Appl. No.: 199,919

[22] Filed: May 27, 1988

[30] Foreign Application Priority Data

Jun. 5, 1987 [DE] Fed. Rep. of Germany ....... 3718913

[51] Int. Cl.⁴ .......................... H01R 4/44; H01R 4/50
[52] U.S. Cl. ................... 439/431; 439/783; 439/864
[58] Field of Search .............. 439/415, 431, 725–729, 439/863, 864, 790, 783, 806, 429, 770, 772–774; 128/419 P

[56] References Cited

U.S. PATENT DOCUMENTS

| | | | |
|---|---|---|---|
| 928,857 | 7/1909 | Donnelly | 439/864 |
| 1,738,157 | 12/1929 | Thurber | 439/770 |
| 2,590,789 | 3/1952 | Noyes | 439/864 |
| 2,763,847 | 9/1956 | Hubbell | 439/736 |
| 3,042,896 | 7/1962 | Doktor | 439/712 |
| 4,103,984 | 8/1978 | Mixon, Jr. | 439/415 |
| 4,142,532 | 3/1979 | Ware | 128/419 P |
| 4,202,592 | 5/1980 | Rullier et al. | 128/419 P |
| 4,507,008 | 3/1985 | Adl et al. | 439/863 |

FOREIGN PATENT DOCUMENTS

| | | | |
|---|---|---|---|
| 671033 | 12/1929 | France . | |
| 1020724 | 2/1953 | France . | |
| 0065961 | 3/1969 | German Democratic Rep. | 439/864 |
| 0323420 | 1/1930 | United Kingdom | 439/864 |
| 904398 | 8/1962 | United Kingdom . | |

*Primary Examiner*—Gary F. Paumen
*Attorney, Agent, or Firm*—Hill, Van Santen, Steadman & Simpson

[57] ABSTRACT

A connector arrangement for a lead for an implantable stimulation device, such as a heart pacemaker, has a receptacle in which a proximal end of a lead is received and a fixing element which is disposed tangentially relative to the proximal end of the lead. The fixing element can assume a first position which provides enough clearance in the receptacle to permit insertion of the proximal end of the lead, and a second position wherein the fixing element forces the proximal end of the lead tightly against a portion of the wall of the receptacle, so that the proximal end is held tightly in the receptacle to make a reliable mechanical and electrical connection. The arrangement permits the housing of the stimulation device to have a small thickness dimension.

9 Claims, 2 Drawing Sheets

CONNECTOR ARRANGEMENT FOR A LEAD FOR AN IMPLANTABLE STIMULATION DEVICE

BACKGROUND OF THE INVENTION

1. Field of the Invention

The present invention is directed to a connector arrangement for making an electrical or mechanical connection of the proximal end of a lead to a terminal of an implantable stimulation device, such as a heart pacemaker, including means for fixing the proximal end of the lead in the terminal.

2. Description of the Prior Art

Various types of connector arrangements are known for use with implantable heart pacemakers for the purpose of mechanically and electrically connecting a proximal end of a lead to the terminal portion of the pacemaker housing. A connector arrangement is described in German OS No. 29 14 034 corresponding to U.S. Pat. No. 4,142,532, wherein the proximal end of the lead is received in a receptacle in the terminal portion of the housing, and set screws are provided in the terminal which hold the proximal end in the receptacle. These set screws extend radially and perpendicularly relative to the proximal end of the lead. As a result of this arrangement, the terminal portion, and thus the entire heart pacemaker, is relatively thick, so that it may be visible at the skin surface after implantation, which can be disturbing for the user.

SUMMARY OF THE INVENTION

It is an object of the present invention to provide a connector arrangement for an implantable stimulation device which permits the terminal portion, an thus the entire stimulation device, to be maintained as thin as possible.

The above object is achieved in accordance with the principles of the present invention in a connector arrangement having a fixing means for holding the proximal end of the lead in a receptacle in the terminal, the fixing means extending tangentially relative to the proximal end of the lead. As used herein the term "tangential" encompasses all arrangements of the proximal end of the lead with the fixing means, regardless of the angle which the axis of the proximal end and the axis of the fixing means make relative to each other. For the purposes of the present invention, it is important only that the surfaces of the proximal end of the lead and of the fixing means touch each other. This means that the receptacle in the terminal in which the proximal end of the lead is received must be slightly bigger than the proximal end of the lead, i.e., a small amount of clearance must be present.

In one embodiment of the invention, the fixing means is a sleeve which is deformable by an expansion element introducible into the sleeve. The clearance of the receptacle permits the proximal end of the lead to be loosely inserted in the receptacle, at which time the expansion element and the sleeve are in a first position which does not disturb the clearance. The expansion element is subsequently introduced into the sleeve, causing the sleeve to deform to a second position which forces the proximal end of the lead against the wall of the receptacle to provide a firm mechanical and electrical connection. This arrangement may be used with a single lead, or to simultaneously retain the two leads of a bipolar lead using a single fixing means. If a bipolar lead is used, the sleeve will be disposed between the receptive proximal ends of each of the leads, and expands toward each of those proximal ends as the expansion element is introduced.

In another embodiment of the invention, the fixing means is a peg extending tangentially to the proximal end of the lead which has a first position which does not disturb the clearance of the proximal end of the lead in the receptacle, thus permitting a loose joining of the proximal end of the lead and the receptacle. The peg can then be moved to a second position which causes a rigid mechanical connection of the proximal end of the lead in the receptacle. This embodiment requires only an opening, which is simple to manufacture, be provided for the peg in the terminal portion of the stimulation device.

In a further modification of this embodiment, the peg may have a flattened area. The flattened area of the peg faces toward the lead when the peg is in the first position, and the peg is rotated by about 90° through 180° to the second position, at which point the flattened area is no longer adjacent the proximal end of the lead.

In a further embodiment, the peg may have an eccentrically disposed rotational axis so that in the first position the peg does not interfere with insertion of the electrode lead into the receptacle, and upon rotation about the eccentric axis the peg assumes the second position, which holds the proximal end of the lead in the receptacle.

In another embodiment of the invention, the fixing means may be a screw extending tangentially relative to the proximal end of the lead. In a first position, the end of the screw does not interfere with the clearance of the proximal end of the lead in the receptacle. As the screw is turned to the second position, the end of the screw moves at least partially through the receptacle against the proximal end of the lead, thereby fixing the lead in the receptacle.

As in the previous embodiment, the screw may have a flattened region which faces the proximal end of the lead when the screw is in the first position, and thus does not disturb the clearance, and which is moved away from the proximal end of the lead as the screw is rotated by about 90° through 180° to assume the second position.

In another modification of this embodiment, the hardness of at least the screw thread is lower than the hardness of the section of the proximal end of the lead which comes into contact with the screw. An especially firm fixing of the lead is obtained in this embodiment because as the threaded section of the screw comes into contact with the proximal end of the lead the threaded section is deformed, so that the surfaces of the fixing means and of the proximal end which are against each other when the fixing means is in the second position are relatively large.

DESCRIPTION OF THE PREFERRED EMBODIMENTS

Figure 1:
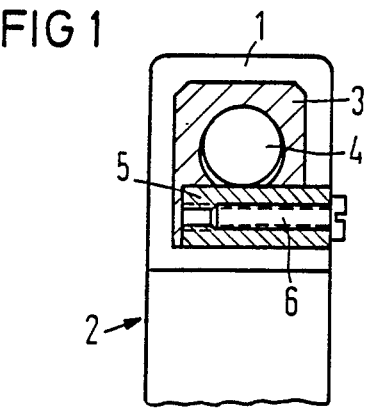
FIG. 1 is a plan view of a terminal portion of a stimulation device having a first embodiment of a conductor arrangement constructed in accordance with the principles of the present invention wherein the fixing means is a sleeve.

FIG. 1 shows a terminal portion 1 of a stimulation device 2, such as a heart pacemaker. The terminal portion 1 has a connector receptacle or socket 3 into which the proximal end 4 of an electrode lead can be introduced. The connector socket serves to electrically connect the stimulation device 2 and the electrode lead. The terminal portion 1 also includes fixing means for electrically and mechanically connecting the proximal end 4 of the electrode lead to the connector socket 3. In this and all embodiments, the fixing means is arranged tangentially relative to the proximal end 4. Additionally, in this and all embodiments the socket 3 is slightly larger than the proximal end 4, so that a clearance exists permitting the proximal end 4 to be loosely inserted into the socket 3.

In the embodiment of FIG. 1, the fixing means is a sleeve 5 having a screw 6 introducible therein, which serves as an expansion element. The sleeve 5 is tangential to the proximal end 4 of the lead. When the screw 6 is not fully introduced into the sleeve 5, the sleeve 5 assumes an undeformed, first position which does not disturb the clearance between the proximal end 4 and the socket 3. As the screw is rotated and becomes fully introduced into the sleeve 5, the sleeve 5 expands to a second position, holding the proximal end 4 within the socket 3 to make a firm electrical and mechanical connection.

Figure 2:
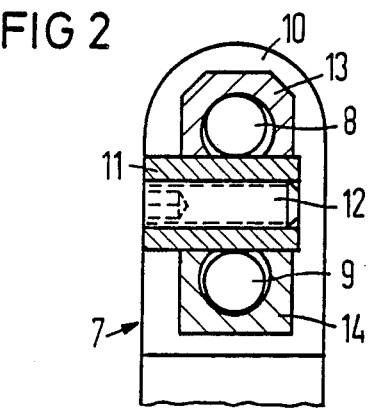
FIG. 2 is a plan view of a bipolar terminal for a stimulation device having a connector arrangement constructed in accordance with the principles of the present invention wherein the fixing means is a sleeve.

The same embodiment for the fixing means is shown in a bipolar stimulation device 7 in FIG. 2. The bipolar stimulation device has a lead with two proximal ends 8 and 9, both introduced into the terminal portion 10. A fixing means consisting of a sleeve 11 and a screw 12 is disposed between the ends 8 and 9. The screw 12 is shown in FIG. 2 fully introduced into the sleeve 11, so that the sleeve is in the expanded, second position thereby forcing both of the ends 8 and 9 against the respective walls of the sockets 13 and 14 to hold the ends 8 and 9 therein.

Figure 3:
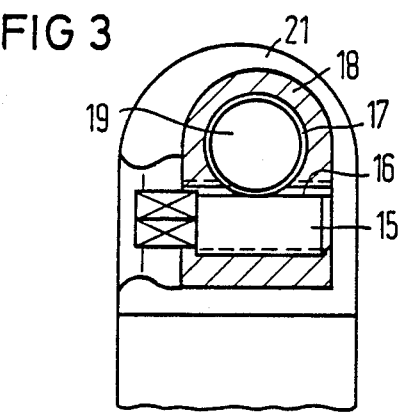
FIGS. 3 and 4 are plan views of the terminal portion of a stimulation device having a second embodiment of a connector arrangement constructed in accordance with the principles of the present invention wherein the fixing means is a screw, respectively showing the fixing means in first and second positions.
Figure 4:
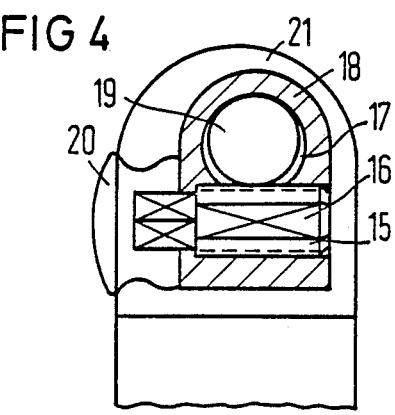

In the embodiments shown in FIGS. 3 and 4, the fixing means is a screw 15 having a flattened area 16. When the screw 15 is in a first position so that the flattened area 16 is opposite the opening 17 of the socket 18, the proximal end 19 of the lead can be plugged into the opening 17. When the screw 15 is rotated by about 90°, as shown in FIG. 4, the end 19 is pressed against the socket 18 and is fixed in this position. A cover cap 20 may be provided so that no body fluid can penetrate into the terminal portion 21 after implantation.

Figure 5:
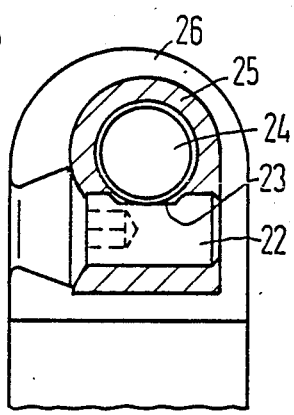
FIGS. 5 and 6 are plan views of a terminal portion of a stimulation device having a third embodiment of a connector arrangement constructed in accordance with the principles of the present invention wherein the fixing means is a peg, respectively showing the fixing means in first and second positions.
Figure 6:
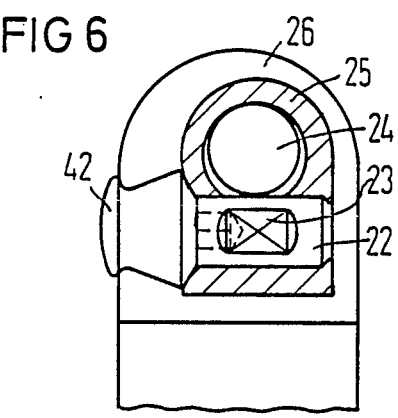

As shown in FIG. 5, the fixing means is a peg 22, which has a flattened region 23. When the peg is in the first position shown in FIG. 5, a proximal end 24 of a lead can be introduced into the socket 25 of a terminal portion 26. When the peg 22 is rotated by about 90°, as shown in FIG. 6, the proximal end 24 is firmly held in the socket 25. Again, a cover cap 42 may be provided to prevent body fluid from penetrating into the terminal portion 26.

Figure 7:
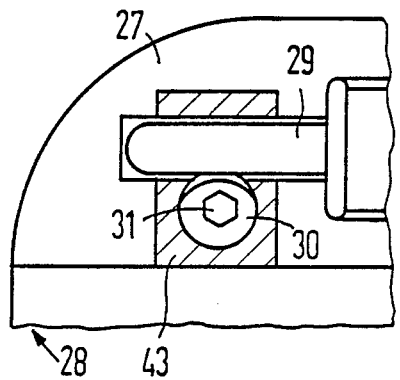
FIGS. 7 and 8 are side views of a terminal portion of a stimulation device having a fourth embodiment of a connector arrangement constructed in accordance with the principles of the present invention wherein the fixing means is eccentrically mounted, respectively showing the fixing means in first and second positions.
Figure 8:
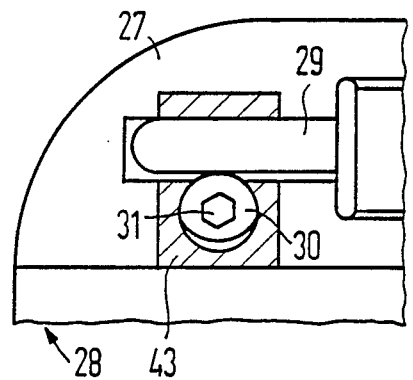

Another embodiment is shown in FIGS. 7 and 8, wherein the fixing means is a eccentrically mounted peg 30. The peg 30 has an eccentric rotational axis 31. In the position of the peg 30 shown in FIG. 7, the proximal end 29 of a lead can be plugged into a connector socket 43 of a terminal portion 27. By turning the peg 30, for example, by 180°, the proximal end 29 is pressed against the connector socket 43, as shown in FIG. 8.

Figure 9:
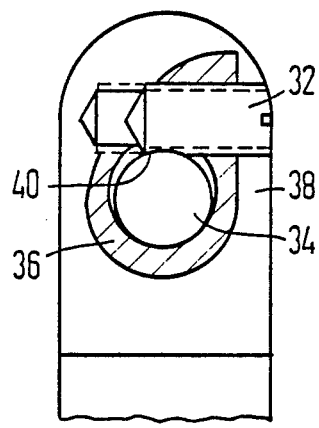
FIGS. 9 and 10 are plan views of a terminal portion of a stimulation device having a fifth embodiment of a connector arrangement constructed in accordance with the principles of the present invention showing the arrangement disposed at different positions relative to the terminal portion.

In the embodiment of FIG. 9, a screw 32 is used as the fixing means. The threads of the screw 32 presses against the surface of a proximal end 34 as the screw 32 is rotated into a threaded bore. The hardness of the threads of the screw 32 may be lower than the hardness of a section 40 of the end 34 which comes into contact with the screw 32. The threads thus become deformed, making a relatively large contact surface.

Figure 10:
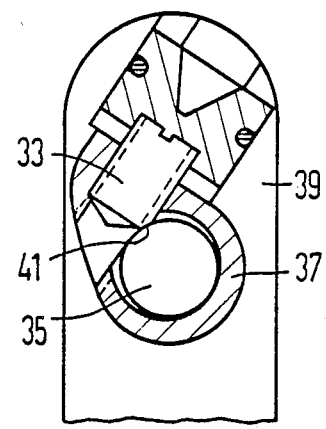

Another embodiment wherein the fixing means is a screw is shown in FIG. 10. In this embodiment, a screw 33 is arranged obliquely in a terminal portion 39, but otherwise operates as the embodiment of FIG. 9. As the screw 33 is rotated, the threads thereof come into contact with a portion 41 of a proximal end 35 of a lead. It is also possible to dispose the fixing means parallel to the axis of the proximal end of the lead, as long as the respective surfaces of the fixing means and the proximal end of the lead remain in tangential contact. The rotating elements of the fixing means may have, for example, a hexagonal head, a socket cap head, or a slotted head.

Although modifications and changes may be suggested by those skilled in the art it is the intention of the inventors to embody within the patent warranted hereon all changes and modifications as reasonably and properly come within the scope of their contribution to the art.

We claim as our invention:

1. In an implantable stimulation device having an electrode lead with a proximal end and a terminal portion of said device having a socket in which said proximal end of said lead is received, the improvement being a connector arrangement comprising:

means for fixing said proximal end of said lead in said socket to make a rigid mechanical and electrical connection, said means for fixing having a longitudinal axis; and means in said terminal portion of said device for receiving said means for fixing such that the longitudinal axis thereof is tangential relative to said proximal end of said lead and substantially normal to the direction of insertion of said lead into said socket.

2. The improvement of claim 1, wherein said means for fixing is a peg in said means for receiving, said peg having a first position in said means for receiving which does not interfere with insertion of said proximal end of said lead into said socket, and a second position in said means for receiving in contact with said proximal end of said lead to fix said proximal end in said socket.

3. The improvement of claim 2, wherein said peg has a flattened region, and wherein said flattened region is disposed adjacent said proximal end when said peg is in said first position, and faces away from said proximal end of said lead when said peg is in said second position.

4. The improvement of claim 2, wherein said peg has an eccentric rotational axis so that rotation of said peg about said eccentric rotational axis moves said peg from said first position to said second position.

5. The improvement of claim 1, wherein said means for fixing is a screw in said means for receiving, said screw having a first position in said means for receiving which does not interfere with the insertion of said proximal end of said lead into said socket, and having a second position in said means for receiving in contact with said proximal end of said lead to fix said proximal end in said socket.

6. The improvement of claim 5, wherein said screw has a flattened region, and wherein said flattened region is adjacent said proximal end of said lead when said screw is in said first position, and faces away from said proximal end of said lead when said screw is in said second position.

7. The improvement of claim 5, wherein said screw has a screw thread and wherein said proximal end of said lead has a region in contact with said screw thread when said screw is in said second position, said screw thread having a hardness which is lower than the hardness of said region of said proximal end of said lead.

8. In an implantable stimulation device having an electrode lead with a proximal end and a terminal portion of said device having a socket in which said proximal end of said lead is received, the improvement being a connector arrangement comprising:
   a deformable sleeve mounted in said terminal portion of said device tangentially to said proximal end of said lead in said socket, said sleeve initially having an underformed first position which does not interfere with insertion of said proximal end of said lead into said socket; and
   means for expanding said sleeve to a second position in contact with said proximal end of said lead in said socket to fix said proximal end of said lead in said socket so that said lead and said socket are in rigid mechanical and electrical connection.

9. The improvement of claim 8, wherein said means for expanding is a screw received in said sleeve.

* * * * *